United States Patent [19]

Becker

[11] Patent Number: 4,863,741

[45] Date of Patent: Sep. 5, 1989

[54] TABLET COMPOSITION FOR DRUG COMBINATIONS

[75] Inventor: Wallace E. Becker, Raymond, Wis.

[73] Assignee: Abbott Laboratories, Abbott Park, Ill.

[21] Appl. No.: 303,012

[22] Filed: Jan. 30, 1989

Related U.S. Application Data

[63] Continuation of Ser. No. 47,545, May 5, 1987, abandoned, which is a continuation of Ser. No. 715,694, Mar. 25, 1985, abandoned.

[51] Int. Cl.⁴ .................. A61K 9/20; A61K 9/26; A61K 31/18; A61K 31/71

[52] U.S. Cl. .................. 424/465; 424/488; 424/489; 514/29; 514/601; 514/781

[58] Field of Search .................. 424/465, 488, 489; 514/29, 601, 781

[56] References Cited

U.S. PATENT DOCUMENTS

| | | | |
|---|---|---|---|
| 2,099,402 | 11/1937 | Keller | 167/82 |
| 2,798,024 | 7/1957 | Zapapas et al. | 514/29 |
| 2,853,420 | 9/1958 | Lowey | 167/82 |
| 2,866,735 | 12/1958 | Himelick | 514/29 |
| 2,928,770 | 3/1960 | Bardani | 167/82 |
| 2,953,497 | 9/1960 | Press | 167/82 |
| 2,996,431 | 8/1961 | Barry | 167/82 |
| 3,081,233 | 3/1963 | Enz et al. | 514/29 |
| 3,115,441 | 12/1963 | Hermelin | 167/82 |
| 3,119,742 | 1/1964 | Heimlich et al. | 167/82 |
| 3,488,418 | 1/1970 | Holliday | 424/35 |
| 3,860,733 | 1/1975 | Morse et al. | 424/35 |
| 3,865,935 | 2/1975 | Amann | 514/29 |
| 3,883,647 | 5/1975 | Geller | 424/15 |
| 3,891,755 | 6/1975 | Mehta | 514/29 |
| 3,906,086 | 9/1975 | Guy et al. | 424/20 |
| 3,922,338 | 11/1975 | Estevenel et al. | 424/21 |
| 3,927,194 | 12/1975 | Geller | 424/15 |
| 3,954,959 | 5/1976 | Pedersen | 424/21 |
| 3,961,041 | 6/1976 | Nishimura et al. | 424/35 |
| 4,025,613 | 5/1977 | Guy et al. | 424/21 |
| 4,076,804 | 2/1978 | Singiser et al. | 514/29 |
| 4,079,125 | 3/1978 | Sipos | 424/35 |
| 4,153,677 | 5/1979 | John | . |
| 4,173,626 | 11/1979 | Dempski et al. | 424/19 |
| 4,250,166 | 2/1981 | Maekawa | 424/81 |
| 4,259,315 | 3/1981 | Lippmann et al. | 424/37 |
| 4,289,751 | 9/1981 | Windheuser | 514/29 |
| 4,340,582 | 7/1982 | Kriesel et al. | 514/29 |
| 4,370,313 | 1/1983 | Davies | 424/32 |
| 4,415,547 | 11/1983 | Yu et al. | 424/21 |
| 4,432,966 | 2/1984 | Zeitoun et al. | 424/21 |
| 4,434,152 | 2/1984 | Horvath et al. | 424/19 |
| 4,461,759 | 7/1984 | Dunn | 424/22 |
| 4,555,399 | 11/1985 | Hsiao | 424/16 |
| 4,599,326 | 7/1986 | Marvola et al. | 514/29 |

FOREIGN PATENT DOCUMENTS

| | | |
|---|---|---|
| 63266 | 3/1982 | European Pat. Off. . |
| 1598458 | 9/1981 | United Kingdom . |

*Primary Examiner*—Shep K. Rose
*Attorney, Agent, or Firm*—Steven F. Weinstock; Edward H. Gorman, Jr.

[57] ABSTRACT

A tablet providing enhanced delivery of an acid-sensitive drug in conjunction with an acid-stable drug is disclosed. The tablet is made up of a matrix containing a major proportion of an acid-stable drug, and a minor proportion of microcrystalline cellulose. Embedded in the matrix are coated granules containing at least about 90% of an acid-sensitive drug by weight, exclusive of the coating, and having a particle size of from about 10 to about 40 mesh. The granules of acid-sensitive drug have an acid resistant and/or enteric coating selected to dissolve in less than sixty minutes at a pH of 5.5 or greater.

2 Claims, No Drawings

TABLET COMPOSITION FOR DRUG COMBINATIONS

This application is a continuation of application Ser. No. 047,545 filed May 5, 1987, which is a continuation of prior application Serial No. 715,694 filed on March 25, 1985 (both now abandoned).

TECHNICAL FIELD

This invention relates to tablet compositions for enhanced delivery of acid-sensitive drugs in conjunction with acid-stable drugs.

Pharmaceutical products which provide fixed combinations of drugs exhibiting complementary activities are an accepted part of medical practice. However, such drugs are frequently dissimilar chemically, and thus exhibit markedly different patterns of uptake, transport and excretion. Particularly problematic is the administration of a combination of an acid-sensitive drug with an acid-stable drug, and especially when the acid-stable drug has a different gastrointestinal absorption characteristic which precludes the use of conventional tableting and coating technology. In such cases, simple enteric coating will protect the acid-sensitive drug, but will not provide optimal blood levels of both drugs, since onset and rate of uptake of the acid-stable drug will be impaired by the delayed release in the lower G.I. tract. Conversely, a rapidly disintegrating and rapidly dissolving tablet will provide prompt high blood levels of the acid-stable drug, but will also expose the acid-sensitive drug to the low pH of the gastric contents, leading to degradation and reduced drug delivery.

Coated or layered tablets which rely on one or more outer coatings for controlled drug release are also inferior in delivery of these drug combinations, since the entire outer portion must dissolve away before the inner, enteric coated, acid-sensitive drug can be passed on to the lower G.I. tract for absorption. Once in the lower G.I. tract, release of the acid-sensitive drug will be dependent upon the dissolution rate of the enteric coated inner tablet.

An additional problem is encountered when optimal administration of the drug combination is achieved at high dosages, which are at or near the maximum dosage which can be comfortably ingested in tablet or capsule form. In such a case, the size of the tablet or capsule imposes an additional constraint upon the amounts of coatings, fillers, and the like which can be incorporated into the tablet or capsule composition to control dissolution, release rate, etc.

In view of these problems with delivery of such drug combinations, there is still a need for a tablet composition for delivery of an acid-sensitive drug in combination with an acid-stable drug which provides a rapid onset of uptake and a rapid rate of dissolution for both drug components, each at the pH best suited to its administration. It is an object of the present invention to provide such a tablet composition. This and other objects of the invention will be evident from the following disclosure.

BACKGROUND ART

U.S. Pat. No. 2,099,402, issued Nov. 16, 1937 to J. W. Keller describes a pill or tablet designed for delivery of a combination of drugs to animals. According to the '402 patent, the pill or tablet is made containing a desired dose of the drug or drugs, the action of which is desired to come last. Over this pill or tablet, an enteric coating of proper thickness and appropriate composition is applied, followed by a second coat which consists of the dose of the second drug or drugs. Over all this, if desired, a suitable finishing coat may be placed.

U.S. Pat. No. 2,853,420, issued Sept. 23, 1958 to H. Lowey describes ethyl cellulose coatings for shaped medicinal preparations. The '420 patent provides for a medically active shaped preparation, containing a number of substantially round medically inactive granulated carriers, each having an impregnation of a solution of therapeutically active material in ethyl cellulose. Upon the impregnation a number of action-delaying ethyl cellulose coatings are present, the number of coatings on at least some of the carriers being different from the number of coatings on the remaining carriers by at least 25. Each of the coatings is substantially not thicker than 0.1% of the radius of the carrier, and 25 coatings contain a total amount of coating material of the order of 1% of the weight of the inactive carrier.

U.S. Pat. No. 2,928,770, issued Mar. 15, 1960 to F. M. Bardani describes a sustained action pill. The sustained action pill of Bardani is formed of layers of medicament separated by control coatings. Each coating includes a porous membrane, initially having a substance closing its pores, to control the flow of alimentary fluids therethrough to the medicament. The time each coating withstands the fluids before becoming porous and the rate of flow of fluids through the coating is determined by its composition and the manner in which it is formed on the medicament layers. Upon subjection of the sustained action pill to alimentary fluids, the material closing the pores is gradually removed and fluids moving through the resultant permeable membrane leach medicament therethrough. Before one medicament layer is dissolved, the next coating is wetted by the fluids to initiate opening of its pores.

U.S. Pat. No. 2,953,497, issued Sept. 20, 1960 to H. A. Press, relates to shaped medicinal preparations, such as tablets, comprising particles or granules of two or more kinds having different dispersion times in the system of the patient to which the preparation is administered. According to the '497 patent, granules consisting, for example, of sugar and cornstarch and granulated with corn syrup are prepared in a coating pan with the application of heat. The therapeutically active ingredients are used in the form of solutions containing a minimum amount of solvent, which are introduced into the uncoated granules or are applied to the granules between the first and last coatings thereof with shellac or cellulose acetate phthalate. A batch of granules is divided into two or more portions which are then treated separately by coating and/or impregnation with different solutions of a binder. The granule portions, having different binder coatings, are combined and compressed to the desired shape and weight, after being mixed with a solid diluent for protecting granules from being crushed during compression.

U.S. Pat. No. 2,996,431, issued Aug. 15, 1961 to R. H. Barry, relates to pharmaceutical tablets which can be disintegrated into a mass of small-size particles by the pressure of the thumb on the tablet and against a table or other surface in a single operation without danger of injury. Barry found that an otherwise crush-resistant tablet can be made friable under thumb pressure by incorporating therein a certain quantity of small pellets of more or less rounded shapes, such as spheroid, ellipsoid, and ovoid forms.

U.S. Pat. No. 3,115,441, issued Dec. 24, 1963 to V. M. Hermelin, relates to timed release pharmaceutical preparations in tablet form, comprising a plurality of finely divided hard particles of a drug, each particle being individually coated with a permeable solution-resistant coating, the particles being dispersed throughout a compressed matrix consisting predominantly of the same drug. In use, the tablet per se disintegrates almost immediately and the initial dosage comprising the matrix is absorbed. The hard particles, however, resist disintegration for about three hours, after which the drug begins to leach out at a steady, attenuated rate which offsets the rate at which the drug disappears from the system.

U.S. Pat. No. 3,119,742, issued Jan. 28, 1964 to K. R. Heimlich and D. R. MacDonnell, relates to a method of making high dosage sustained release pharmaceutical pellets. In the method of Heimlich and MacDonnell, crystals of medicaments are coating with additional medicament to produce smooth, spherical pellets which are divided into a plurality of groups, each of which groups is coated with a slowly digestible or dispersable time delay coating to provide pellets of a diameter from about 0.1 to about 2.0 millimeters, containing from 85 to 95% active medicament and providing different times of release of the medicament on ingestion. The resulting pellets are combined in standard gelatin capsules.

U.S. Pat. No. 3,906,086, issued Sept. 16, 1975 to Guy et al. relates to a timed release aspirin composition. The composition of the '086 patent is made by coating particles of aspirin prior to tableting with a coating solution containing cellulose acetate phthalate. The tablet so produced remains substantially intact while in the stomach and dissolves at a slow, controlled rate in the intestinal tract. Aspirin tablets providing both immediate pain relief and timed release are produced by pressing separate layers of aspirin particles coated in this manner and ordinary uncoated aspirin into a double-layered tablet.

U.S. Pat. No. 4,025,613, issued May 24, 1977, also to Guy et al., is a divisional of the same application.

U.S. Pat. No. 4,173,626, issued Nov. 6, 1979 to Dempski et al. relates to a sustained release indomethacin composition. In the product of the '626 patent, a pellet formulation encapsulated in a hard gelatin capsule is used. A portion of the pellets is uncoated for immediate and rapid release of indomethacin for elevating the plasma level. The remainder of the pellets are coated with a polymer to sustain the plasma level. The uncoated and coated pellets may be mixed with non-medicated pellets as a capsule filler.

U.S. Pat. No. 4,250,166, issued Feb. 10, 1981 to Maekawa et al. relates to a long-acting cefalexin preparation. The preparation involves a portion of enteric coated cefalexin administered concurrently with a plain, quick releasing cefalexin. The coated preparation is preferably coated in particle form, and when administered orally, exists in a particle form in the stomach. Preferably, the coating layer is made from a coating material having a dissolution pH of from 5.5 to 6.5.

European Patent No. 63,266, filed Mar. 31, 1982 and based on a German priority document dated Apr. 7, 1981 relates to long-acting preparations for maintenance therapy with the calcium antagonist gallopamil and verapamil. The compositions are standard and contain a fast-release fraction and a slow-release fraction.

DISCLOSURE OF THE INVENTION

This invention provides a tablet for enhanced oral delivery of an acid-sensitive drug in conjunction with an acid-stable drug. The tablet composition comprises a matrix comprising a major proportion of an acid-stable drug, and a minor proportion of microcrystalline cellulose. The matrix has embedded therein coated granules, preferably containing at least about 90% of an acid-sensitive drug by weight, exclusive of the coating, and having a particle size of from about 10 to about 40 mesh. The coating is an enteric and/or acid resistant coating selected to dissolve in less than sixty minutes at a pH of 5.5 or greater. The overall tablet has a nonenteric coating, a hardness sufficient to resist a crushing or fracturing pressure of at least about 15 kg/in$^2$ and a disintegration time of less than thirty minutes in an aqueous medium.

Acid-stable Matrix

This tablet is designed for delivery of a maximal dose of both acid-stable and acid-sensitive drug, and for providing the most rapid possible absorption of each. To this end, the tablet contains a minimal quantity of inert ingredients and tableting aids with the exception of microcrystalline cellulose. In general, the inert ingredients other than microcrystalline cellulose will constitute less than 15%, and preferably less than 10%, of the matrix composition. The matrix will contain at least 50% and preferably at least 60% of the acid-stable drug. The balance of the matrix composition, generally from 10 to 45% by weight, is microcrystalline cellulose. The microcrystalline cellulose serves its conventional function as a disintegration aid for the tablets. But more importantly, it also serves to protect the granules of acid-sensitive drug, as described hereinafter, from fracture during the tableting process, as disclosed in the copending application of Becker, "Pharmaceutical Tableting Method", Ser. No. 715,693, filed Mar. 25, 1985, the disclosures of which are incorporated herein by reference.

The inert ingredients are selected and formulated to provide a tablet disintegration time of less than 30 minutes, which disperses the acid-stable drug for uptake by the system. In addition, it disperses the coated granules of acid-sensitive drug, as described herein, for passage from the stomach to higher pH regions of the G.I. tract, where their absorption can take place.

At the same time, the tablets are formed under high compression forces to provide a hardness sufficient to resist an applied fracturing pressure of at least about 15 kg/in$^2$ to prevent their mechanical disintegration during the final coating step and subsequent handling. Preferably, the tablets are compressed to a hardness to resist pressures of at least about 20 kg/in$^2$, most preferably about 25 kg/in$^2$.

The finished tablets have a nonenteric coating which preferably consists of polyvinylpyrrolidone and a cellulosic polymer, to provide lubricity needed to aid in swallowing the tablet. This is particularly important where large tablet sizes are necessary to provide maximum doses of the drug combination. The coating also gives the tablet an aesthetically acceptable appearance.

Acid-sensitive Granules

Embedded within the matrix of the tablet, as described above, are coated granules of the acid-sensitive drug. To maximize delivery of the acid-sensitive drug, the granules are formed substantially completely from the acid-sensitive drug, i.e., about 90% or greater acid-sensitive drug by weight prior to coating.

The granules have a particle size of from about 10 to about 40 mesh. It has been determined that particles in this size range are rapidly passed from the stomach into the duodenum and beyond. Thus, the granulation size is selected not only to facilitate tableting, but to permit uptake of the acid-sensitive drug at the fastest possible rate.

The granules have a coating which protects the acid-sensitive drug from the action of stomach acids. The coating is also selected to provide rapid release of the acid-sensitive drug at the higher pH of the duodenum and small intestine. Thus, the enteric coating is selected to dissolve in less than sixty minutes at a pH of 5.5, or greater, which is the pH typically present in the duodenum and small intestine. Enteric and acid resistant coating materials include without limitation polyvinyl acetate phthalate, cellulose acetate phthalate, hydroxypropylmethylcellulose phthalate, and shellac, as well as numerous other polymers familiar to those of ordinary skill in the art of pharmaceutical manufacture.

In use, each of the above-described features of the tablet composition of this invention cooperates to facilitate enhanced delivery of the acid-sensitive/acid-stable drug combination. Upon ingestion, the nonenteric coating of the tablet as a whole facilitates swallowing and transport of the tablet to the stomach for disintegration. This is particularly important in the case of tablets according to this invention, where the tablet is designed to disintegrate rapidly. Difficulty in swallowing or in esophageal transport of the tablet to the stomach could result in premature disintegration of the tablet, which is both unpleasant to the patient and potentially irritating to mucosal lining of the mouth or esophagus.

Rapid disintegration of the tablet upon reaching the stomach provides for immediate dispersion of the acid-stable drug and permits rapid absorption. At the same time, it provides release of the embedded enteric-coated granules of acid-sensitive drug which, because of their size, are readily transported to the duodenum and beyond. Upon reaching the duodenum, the enteric coating on the granules dissolves at the ambient pH, immediately releasing the acid-sensitive drug to an environment in which it is stable and which facilitates its absorption at the high levels provided by the granules, which are 90% or more active ingredient. As stated, the microcrystalline cellulose in the matrix prevents fracture of the coating on the granules, so that undesired release of the acid-sensitive drug in the gastric environment is avoided.

INDUSTRIAL APPLICABILITY

Acid-Sensitive Drug

By "acid-sensitive" is meant drugs which are either degraded, inactivated or nonabsorbable in an acid environment, such as the gastric pH of 1-2. In general, any acid-sensitive drug which is desired to be administered in conjunction with an acid-stable drug can be used in the practice of this invention. Examples of such drugs include without limitation erythromycin, penicillin, clorazepate, digitalis glycosides, cephalosporins, novobiocin and pancreatin.

Acid-Stable Drug

Similarly, any acid-stable drug which is desired to be administered in conjunction with an acid-sensitive drug can be used in the practice of this invention. By "acid-stable" is meant any drug which is not degraded or inactivated by the acid pH of the stomach. These include, for example, the sulfonamide drugs, the belladonna alkaloids, the tetracycline antibiotics, furosemide and probenecid, without limitation.

Binders and Tableting Aids

In general, the binders and tableting aids readily known to those of ordinary skill in the science of pharmaceutical manufacture can be used in the practice of this invention. For example, a variety of stearate tableting aids, starches, gums, waxes, polymers, and the like can be used, within the percentage limits previously specified. An essential tableting aid in the practice of this invention is microcrystalline cellulose, NF, available as Avicel. As stated before, the microcrystalline cellulose is necessary to prevent fracture of the enteric coating on the granules of acid-sensitive drug, which would cause their premature release in the stomach.

The practice of this invention is further illustrated by the following, nonlimiting examples.

EXAMPLE 1

To evaluate the feasibility of a single, non-enteric coated preparation containing erythromycin, the times required for 50% destruction of erythromycin activity $t_{50}$) and 10% destruction of erythromycin activity $t_{90}$) in aqueous solution at 25° C. were calculated as a function of pH from data reported in the literature. Results are indicated in the table below.

TABLE 1

| pH | $t_{50}$ | $t_{90}$ |
| --- | --- | --- |
| 3.0 | 10.0 min. | 1.52 min. |
| 3.5 | 34.7 min. | 528 min. |
| 4.0 | 1.67 hours | 15.2 min. |
| 4.5 | 5.79 hours | 52.8 min. |
| 5.0 | 16.7 hours | 2.54 hr. |
| 5.5 | 2.41 days | 8.8 hr. |
| 6.0 | 6.96 days | 1.06 days |

It was concluded from these calculations that erythromycin could not be subjected to the pH of the gastric contents via a non-enteric coated combination drug product and still maintain acceptable dosage strength, i.e., 90% of the intended dose. Erythromycin can be considered representative of acid-sensitive drugs in this regard.

EXAMPLE 2

The bioavailability of the acid-stable drug sulfamethoxazole (SMZ) in two experimental formulations was evaluated in 24 healthy adult volunteers. The study involved a single-dose, two period crossover design. One of the formulations was a commercially available SMZ preparation, crushed and recompressed into tablets to disguise its identity. The other was the same re-tableted product, but with an enteric coating.

Each subject received both preparations, one in each study period. One tablet containing 500 mg of sulfamethoxazole was administered with four ounces of water once during each study period. Twelve of the subjects received the preparations while fasting, and twelve of the subjects received the preparation after a standardized meal.

Blood samples were drawn each hour for the first six hours after ingestion, and at 8, 10, 12, 24, 6 and 48 hours after ingestion, and analyzed for SMZ content. Urine samples were also obtained at regular intervals and analyzed for SMZ.

The results indicated that the absorption of SMZ from the enteric-coated tablets was delayed in comparison with the uncoated tablets under both fasting and nonfasting conditions. This relative delay was greater under the nonfasting regimen. Mean serum SMZ levels at most of the sampling times and the means of individual peak concentrations and areas under the concentration-time curves were significantly higher for the uncoated preparation under each regimen. These serum-level results indicate that the enteric coated formulation was less bioavailable than the uncoated formulation, and that enteric coating was detrimental to the bioavailability of sulfamethoxazole tablets. Therefore, a single, completely enteric coated preparation containing both sulfamethoxazole and a drug which requires protection by enteric coating, such as erythromycin, would provide unacceptable delivery of the sulfamethoxazole. Sulfamethoxazole can be considered to be representative of acid-stable drugs in this regard.

EXAMPLE 3

Tablets for the combined administration of erythromycin, an acid-sensitive drug with sulfamethoxazole, an acid-stable drug, are prepared as follows: 500 grams of sulfamethoxazole and 10 grams of a starch derivative are charged into a mass mixer. Ten grams of cornstarch are added along with sufficient water to make a starch paste. This starch paste is used to make a standard granulation tableting, which is dried and sized.

Separately, 275 grams of erythromycin and 10 grams of conventional cellulosic binder are charged into a mass mixer. A solution of 10 grams povidone in water is added, and the mixture is granulated. The granulation is dried and sized in similar fashion to the sulfamethoxazole granulation, to yield particles of 10 to 40 mesh. Oversize and undersize particles are recycled.

Separately, 80 grams of a cellulose phthalate enteric coating polymer, and 8 grams of an alkyl citrate plasticizer are dispersed in a sufficient quantity of acetone and ethanol to make a solution. 0.3 grams of blue dye lake are added, and the dispersion is stirred to mix. The erythromycin granulation is coated with this solution in a particle coater and the resulting coated particles are sized. Separately, a portion of the sulfamethoxazole granulation is charged into a blender. The dried erythromycin coated particles sized to 10 to 40 mesh are added, as well as 200 grams of microcrystalline cellulose, NF and 4 grams of conventional lubricants and glidants. The remainder of the sulfamethoxazole granulation is added and the mixture is blended. This blended material is compressed in a conventional tablet press at applied forces of from 1500 pounds per square inch to 6000 pounds per square inch, into tablets having a weight per 10 tablets of approximately 12 grams.

The hardness of the resulting tablets are measured using a modified Strong-Cobb hardness tester. This tester works by applying a force to the surface of the tablet via a shaped die. The applied force, divided by the surface area of the die-tablet contact area, gives a reading measured in kilograms per square inch. The applied force is gradually increased until the tablet fractures. Hardness is measured at the point just before fracture of the tablet, averaged over ten tablets. In general, large tablets having a hardness sufficient to resist applied fracturing pressures greater than 15 kg/in$^2$ will readily withstand the stresses imposed by conventional commercial packaging and distribution, tablets having a hardness greater than 0 kg/in$^2$ are considered very hard, and tablets having a hardness greater than 25 kg/in$^2$ are considered extremely hard.

Disintegration times for the tablets are determined by performing conventional USP disintegration test procedures, as described in USP XX, Mack Publishing Co., Easton, PA, 1980, pp. 958–960, the disclosures of which are hereby incorporated herein by reference. The USP Disintegration Apparatus (Stoll-Gershberg apparatus) without discs is employed, using distilled water as the aqueous medium. Disintegration time is identified as the time to complete passage of the tablet (as disintegrated) through a 10-mesh screen.

EXAMPLE 4

Erythromycin-sulfamethoxazole tablets prepared in the general manner of Example 3 were evaluated for drug bioavailability in comparison with the combined administration of an enteric coated erythromycin tablet and a non-enteric coated sulfamethoxazole tablet. Two studies were performed, each using a single-dose, three period, crossover design. One compared bioavailability in fasting subjects, the other in nonfasting subjects following a standardized meal. Blood samples and urine samples were obtained and analyzed for both erythromycin and sulfamethoxazole, in a manner similar to Example 2.

Analysis of variance was performed on serum levels for each of the sampling times, individual peak concentrations, and areas under the concentration-time curves for both erythromycin and sulfamethoxazole.

The results of the studies indicated that the erythromycin-sulfamethoxazole combination tablet prepared according to this invention was at least bioequivalent to the two separate tablets in both fasting and nonfasting subjects, and provided greater bioavailability for erythromycin in fasting subjects.

What claimed is:

1. A method of administering erythromycin and a sulfonamide drug in a single tablet and improving the bioavailability of erythromycin in fasting subjects, the tablet matrix having distributed therein at least 60% sulfonamide drug and granules containing at least about 90% erythromycin by weight wherein the granules have a particle size of from about 10 to about 40 mesh and an enteric or acid-resistant coating which dissolves in less than 60 minutes at a pH of 5.5 or greater; the tablet having a nonenteric coating and a disintegration time of less than 30 minutes, the improvement comprising:

adding from 10% to 45% microcrystalline cellulose to the tablet matrix to prevent fracturing of the enteric coated erythromycin granules and provide a tablet hardness sufficient to resist an applied fracturing pressure of at least about 15 kg/in$^2$.

2. In a pharmaceutical tablet having a matrix of at least 60% sulfonamide drug, the matrix having distributed therein granules containing at least about 90% erythromycin by weight, and having a particle size of from about 10 to 40 mesh, the granules having an enteric or acid-resistant coating which dissolves in less than 60 minutes at a pH of 5.5 or greater, the tablet having a nonenteric coating and a disintegration time of less than 30 minutes, the improvement comprising:

the tablet matrix from 10% to 45% microcrystalline cellulose to prevent fracturing of the enteric coated erythromycin granules and provide a tablet hardness sufficient to resist an applied fracturing pressure of at least about 15 kg/in$^2$.

* * * * *